United States Patent [19]  
De Bernardinis et al.

[11] Patent Number: 5,015,745  
[45] Date of Patent: May 14, 1991

[54] PROCESS FOR THE PREPARATION OF 4-DEMETHOXYDAUNOMYCINONE, THE AGLYCONE OF 4-DEMETHOXY-DAUNORUBICIN

[75] Inventors: Silvia De Bernardinis, Milan; Walter Cabri, Limbiate; Tiziano Martinengo, Carpignano Sesia; Franco Francalanci, Novara, all of Italy

[73] Assignee: Farmitalia Carlo Erba S.R.L., Milan, Italy

[21] Appl. No.: 306,559

[22] Filed: Feb. 6, 1989

[30] Foreign Application Priority Data

Feb. 12, 1988 [GB] United Kingdom ............... 8803301

[51] Int. Cl.$^5$ ................ C07C 103/19; C07C 103/75
[52] U.S. Cl. ................................ 552/206; 552/201
[58] Field of Search ............................... 552/206, 201

[56] References Cited

U.S. PATENT DOCUMENTS

| | | | |
|---|---|---|---|
| 3,862,225 | 1/1975 | Conover et al. | 552/203 |
| 4,020,270 | 4/1977 | Arcamone et al. | 552/201 |
| 4,046,878 | 9/1977 | Patelli | 536/17 |
| 4,077,988 | 3/1978 | Arcamone | 552/206 |
| 4,132,721 | 1/1979 | Bernardi | 552/706 |
| 4,495,103 | 1/1985 | Terashima et al. | 552/206 |

FOREIGN PATENT DOCUMENTS 0337665 10/1989 European Pat. Off. ............ 552/201

OTHER PUBLICATIONS

European Search Report EP 89 30 1282.  
Journal of Antibiotics, vol. 33, No. 7, pp. 705–710 (1980).  
Barnett, Anthracene and Anthraquinone, 1921, pp. 261 & 266.

Primary Examiner—Richard L. Raymond  
Assistant Examiner—Raymond Covington  
Attorney, Agent, or Firm—Oblon, Spivak, McClelland, Maier & Neustadt

[57] ABSTRACT

4-Demethoxy-daunomycinone I:

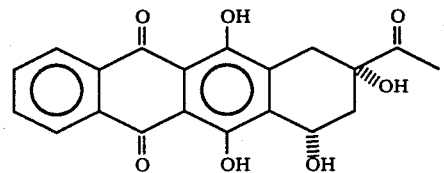

the known aglycone of 4-demethoxy-daunorubicin, is prepared by protecting the 13-keto group of 4-demethyl-daunomycinone, sulfonylating the 4-hydroxy group, reacting the sulfonylated compound with an amine, removing the amino protecting group from the resultant 4-demethyl-4-(protected amino)-13-dioxolanyl-daunomycinone, diazotizing the thus-freed 4-amino group and reducing under mild conditions the resulting diazonium compound.

11 Claims, No Drawings

PROCESS FOR THE PREPARATION OF 4-DEMETHOXYDAUNOMYCINONE, THE AGLYCONE OF 4-DEMETHOXY-DAUNORUBICIN

The present invention relates to a process for preparing 4-demethoxydaunomycinone which has the formula I:

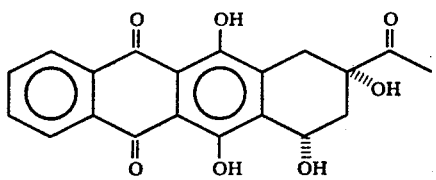

(I)

4-Demethoxydaunorubicin, which is an analogue of the known antibiotic daunorubicin, is a glycoside formed from a tetracyclic aglycone (+) 4-demethoxydaunomycinone (I) and the amino sugar daunosamine. Its utility as a potent antitumor compound is described in Cancer Treatment Report 60 (7): 829–834 (1976) and ibidem 61 (5): 893–894 (1977).

A synthesis of (+) 4-demethoxydaunomycinone is described in U.S. Pat. No. 4,046,878. Another synthesis is based on the preparation of racemic 1,4-dimethoxy-6-hydroxy-6-acetyltetraline, its optical resolution, condensation of the (−) enantiomer with phthalic anhydride and stereoselective introduction of the OH group in position 7 (see U.S. Pat. Nos. 4,077,988 and 4,132,721). According to the present invention, there is provided a process for the preparation of 4-demethoxy-daunomycinone of formula (I):

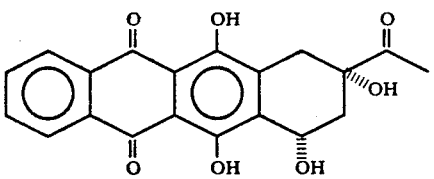

I which process comprises:

(a) protecting the 13-keto group of 4-demethyl-daunomycinone of formula (2):

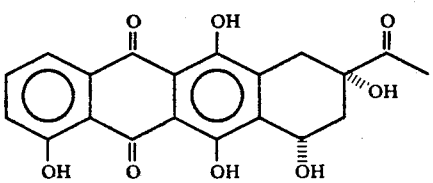

2 by treatment with ethylene glycol;

(b) reacting the resultant 4-demethyl-13-dioxolanyl-daunomycinone of formula (3):

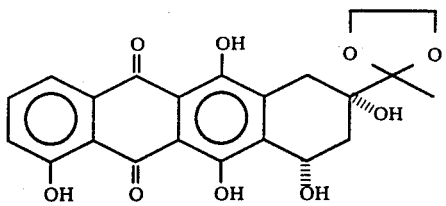

3 with a sulfonyl chloride of formula II:

wherein R represents an alkyl group of from 1 to 10 carbon atoms optionally substituted by one or more halogen atoms or an aryl group optionally substituted by halogen, alkyl, alkoxy or nitro, in the presence of N,N-diisopropylethylamine and a catalytic amount of 4-dimethylamino-pyridine;

(c) reacting the resultant sulfonated 4-demethyl-13-dioxolanyl-daunomycinone of formula (4):

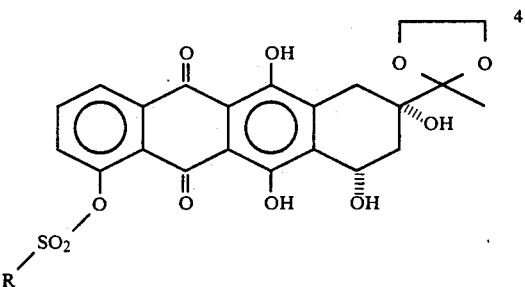

4

wherein R is as defined above, with an amine of formula III:

$R^1(R^2)CH-NH_2$ (III)

wherein $R^1$ and $R^2$ each independently represents a hydrogen atom or a phenyl group bearing one or more alkoxy groups;

(d) removing the amino protecting group from the resultant 4-demethyl-4-(protected amino)-13-dioxolanyl-daunomycinone of formula (5):

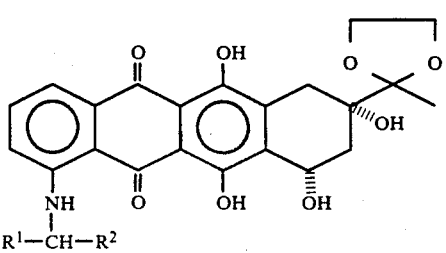

5 wherein $R^1$ and $R^2$ are as defined above;

(e) diazotising the 4-amino group fo the resultant 4-demethoxy-4-amino-daunomycinone of formula (6):

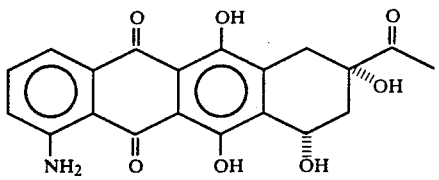

and (f) reducing the resultant diazo-derivative of formula (7):

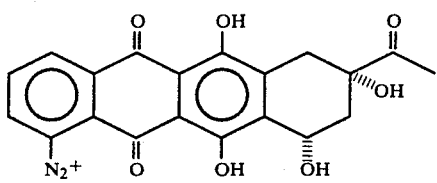

under mild conditions, thereby to obtain 4-demethoxydaunomycinone of formula I.

The 4-demethyl-daunomycinone of formula (2) may be prepared by demethylation of daunomycinone of formula (1):

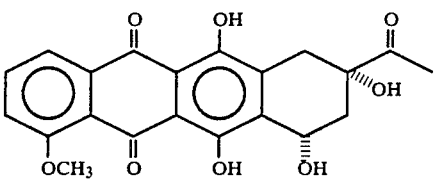

It is therefore possible to provide a process, which may start from the naturally-occurring (+) daunomycinone, which is more efficient and requires less steps than the total chemical synthesis. Moreover the process does not require either optical resolution or chemical purification steps. The intermediates of formulae (3) to (5) are novel and are included in the invention.

The present process is illustrated by the following reaction scheme (Scheme 1). The starting material for the process may be (+) daunomycinone (1). This can be prepared by a suitable hydrolysis of daunorubicin, in its turn obtained by fermentation as described in U.S. Pat. No. 4,012,284. Daunomycinone can be demethylated by treatment with $AlCl_3$ in an inert organic solvent such as nitrobenzene at the reflux temperature to give 4-demethyldaunomycinone which is called also carminomycinone (2). Such a process is described in U.S. Pat. No. 4,188,377.

Step (a) may be effected by treatment with ethylene glycol in the presence of p-toluenesulfonic acid at the reflux temperature. The resultant compound (3) is sulfonated in step (b) at position C4—OH to give compound (4), without any protection of the remaining OH groups. The sulfonating agent is a sulfonyl chloride of formula II:

$$R—SO_2Cl \qquad (II)$$

wherein R represents an alkyl group having from 1 to 10 carbon atoms, a halo or polyhalo such alkyl group or an aryl group optionally substituted by at least one, for example from one to three, substitutents selected from halogen atom(s) and alkyl such as $C_1$-$C_4$ alkyl, alkoxy such as $C_1$-$C_4$ alkoxy and nitro groups. Preferred groups which R may represent are: 4-fluorophenyl and 4-tolyl. Preferably the reaction is carried out in pyridine. It should be stressed that this selective sulfonylation does not affect either the phenolic C6—OH and C11—OH or the benzylic C7—OH only under the conditions of the invention, namely reacting the 4-demethyl-daunomycinone derivative (3) with the sulfonyl chloride in the presence of N,N-diisopropylethlamine and a catalytic amount of 4-dimethylamino pyridine.

The compound (4) thus formed is directly treated in solution in step (c) with an appropriate amine of formula III:

wherein $R^1$ and $R^2$ may each independently represent a hydrogen atom or a phenyl group bearing one or more, for example from 1 to 3, alkoxy groups. The alkoxy group(s) may have from 1 to 4 carbon atoms. Preferred amines of formula

SCHEME 1

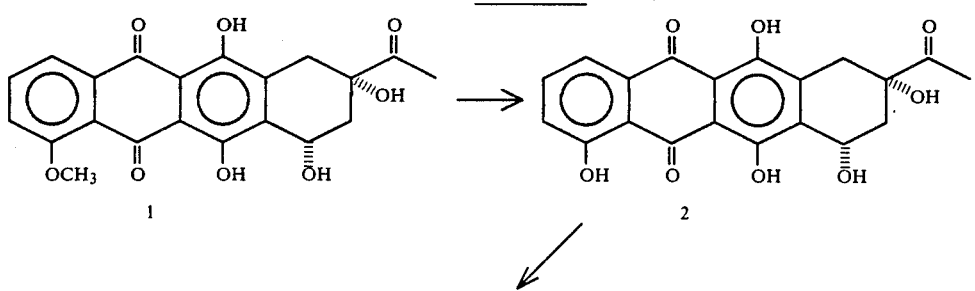

-continued
SCHEME 1

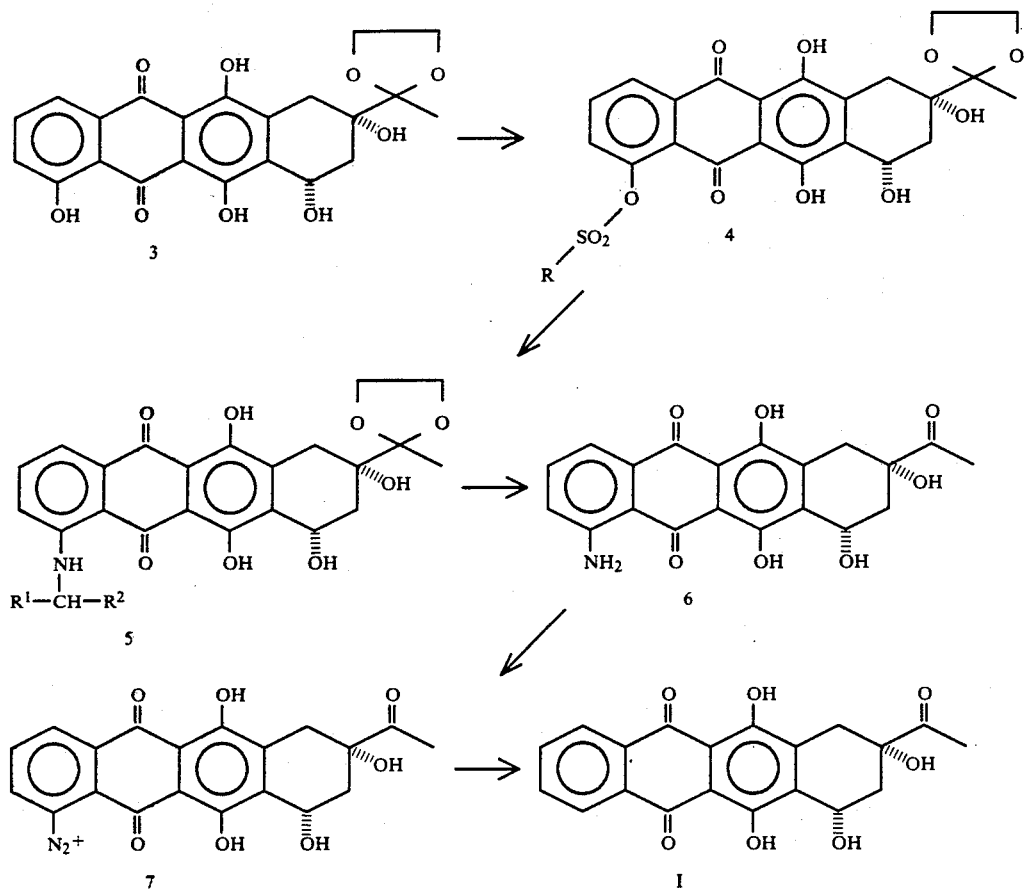

III are 4-methoxybenzylamine and 3,4-dimethoxybenzylamine.

The protected amine of formula (5) can be treated in step (d) with trifluoroacetic acid, for example for three hours at room temperature, in order to liberate the 4-amino derivative (6). Diazotisation in the next step (e) can be effected using sodium nitrite, for example using an aqueous solution of sodium nitrite at from 0° to 5° C. Thus, the acidic solution from step (d), to which water and methylene chloride have been added, can be treated with sodium nitrite to give the diazonium salt (7) which may be extracted in the aqueous phase. Treatment of the aqueous solution with hypophosphorous acid, for example with 50% hypophosphorous acid, affords in step (f) the desired 4-demethoxydaunomycinone (I) of high optical and chemical purity.

4-Demethoxy-daunomycinone is the aglycone moiety of the useful antitumor drug 4-demethoxy-daunorubicin. Accordingly, the present invention further provides a process for preparing 4-demethoxy-daunorubicin of formula IV

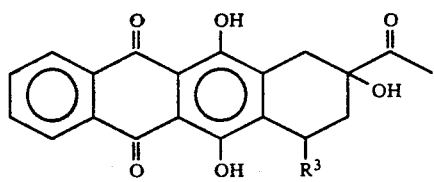

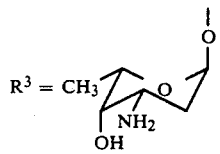

or a pharmaceutically acceptable salt thereof, which process comprises reacting 4-demethoxy-daunomycinone of formula I which has been prepared by the process of the invention with an appropriate sugar derivative and, if desired, converting the 4-demethoxy-daunorubicin thus-obtained into a pharmaceutically acceptable salt thereof.

The sugar derivative may have the formula

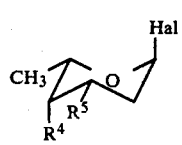

wherein Hal represents a halogen atom, $R^4$ represents a protected hydroxy group and $R^5$ represents a protected amino group. The protecting groups are removed after reaction with the 4-demethoxy-daunomycinone. Preferably Hal is a chlorine atom. The hydroxy group may be protected by a trifluoroacetyl group. The amino group may be protected by a trifluoroacetyl group also.

The resulting 4-demethoxy-daunorubicin or pharmaceutically acceptable salt thereof may be formulated, for example for use as an antibiotic or as an antitumor agent, as a pharmaceutical composition comprising a pharmaceutically acceptable carrier or diluent.

The following Examples illustrate the invention.

EXAMPLE 1

4-Demethyldaunomycinone (2)

To a solution of 15.04 g (37.8 mmol) of daunomycinone (1) in 1.4 L of methylene chloride under stirring, in a nitrogen atmosphere, 52.8 g (396.4 mmol) of anhydrous aluminium chloride were added portionwise over a period of 1.5 hour. The reaction mixture was refluxed for one hour, then the solvent was distilled off. A solution of 22.8 g (25.4 mmol) of oxalic acid in 200 mL of water cooled at 0° C. was carefully added to the residue and the mixture stirred for two hours at room temperature. The solid was recovered by filtration and washed with water. The product was no further purified and showed, on HPLC analysis, to be of 83% purity.

| HPLC analysis: | |
|---|---|
| Column: MERCK 18/7 μm (250 × 4.2 mm), | |
| Mobile phase: | |
| A - 0.01 M sodium heptansulfonate/0.02 M phosphoric acid | 6 |
| Acetonitrile | 4 |
| B - Methanol | 7 |
| Acetonitrile | 3 |
| Gradient: from 20% B to 70% B in 25 min, | |
| Flow rate: 1.5 mL/min, | |
| Detector: UV at 254 nm. | |

TLC on Kieselgel plate F 254 (Merck) using Chloroform/Acetone (8:2 by volume) Rf=0.58

EXAMPLE 2

4-Demethyl-13-dioxolanyl-daunomycinone (3)

To a suspension in benzene (400 mL) of the crude 4-demethyldaunomycinone (2), obtained as described in example 1, 30 mL of ethylene glycol and 0.3 g of p.toluene sulfonic acid were added. The reaction mixture was refluxed with azeotropic removal of water for ca. 6 hours. After cooling to room temperature the solid was recovered by filtration and washed with water and ethanol to give, after drying, 11.3 g of (3) (HPLC: 98.3%, conditions as described in example 1). Overall yield from (1): 70%

$^1$H-NMR 300 MHz (in CDCl$_3$): δ=1.42 (3H, s), 1.94 (1H, dd), 2.42 (1H, dt), 2.75 (1H, d), 3.18 (1H, dd), 4.04 (4H, s), 5.20 (1H, dd), 7.25 (1H, d), 7.65 (1H, t), 7.84 (1H, d), 12.18 (1H, s), 12.92 (1H, s), 13.52 (1H, s).

M.S.: m/z =428 (M+, base peak).

TLC on Kieselgel plate F 254 (Merck) using Chloroform/Acetone (8:2 by volume) Rf=0.52

EXAMPLE 3

4-Demethyl-4-p.toluenesulfonyl-13-dioxalanyl-daunomycinone (4)

To a suspension in pyridine (330 mL) of 11.3 g (26.4 mmol) of (3), 22.6 mL (132 mmol) of diisopropylethylamine and 0.65 g (5.3 mmol) of 4-dimethylaminopyridine, a solution of 5.54 g (29 mmol) of p.toluene sulfonyl chloride in 25 mL of pyridine was added dropwise over a 5 minutes period. After stirring for 15 minutes at room temperature the reaction was completed.

The crude product was directly used in the next step.

$^1$H-NMR 300 MHz (in CDCl$_3$): δ=1.45 (3H, s), 1.92 (1H, dd), 2.18 (1H, s), 2.40 (3H, s), 2.34–2.52 (1H, m), 2.70 (1H, d), 3.15 (1H, dd), 4.06 (4H, m), 5.18 (1H, d), 7.28 (2H, d), 7.53 (1H, d), 7.74 (1H, t), 7.82 (2H, d), 8.28 (1H, d), 13.15 (1H, s), 13.48 (1H, s) M.S.: m/z =582 (M+, base peak).

TLC on Kieselgel plate F 254 (Merck) using Chloroform/Acetone (8:2 by volume) Rf=0.62

EXAMPLE 4

4-Demethyl-4-p.methoxybenzylamino-13-dioxolanyl-daunomycinone (5)

To the solution obtained in example 3, maintained at 35° C., 101 mL (792 mmol) of p.methoxybenzylamine were added. The reaction mixture was stirred at 35° C. for 16 hours then cooled to 0° C. and added with 4 L of methylene chloride and 2 L of 10% hydrochloric acid. After separation, the organic phase was washed with water, saturated NaHCO$_3$ and water. The solution was dried over sodium sulfate and the solvent evaporated under reduced pressure. The residue was directly used in the next step.

$^1$H-NMR 300 MHz (in CDCl$_3$): δ=1.50 (3H, s), 1.95 (1H, dd), 2.45 (1H, dt), 2.78 (1H, d), 3.20 (1H, bs), 3.23 (1H, dd), 3.80 (1H, bs), 3.84 (3H, s), 4.08 (4H, s), 4.53 (2H, d), 5.24 (1H, bs), 6.93 (2H, d), 7.03 (1H, d), 7.31 (2H, d), 7.48 (1H, t), 7.63 (1H, dd), 9.80 (1H, t), 13.47 (1H, s), 13.72 (1H, s).

TLC on Kieselgel plate F 254 (Merck) using Chloroform/Acetone (8:2 by volume) Rf=0.70

M.S.: m/z=547 (M+, base peak)

EXAMPLE 5

4-Demethoxydaunomycinone (I)

The crude product obtained as described in example 4 was dissolved in 100 mL of trifluoroacetic acid and stirred for 3 hours at room temperature. The reaction mixture, after neutralization was purified by column chromatography to give (6).

$^1$H-NMR 300 MHz (CDCl$_3$): δ=2.14 (dd, J=4.8, 15 Hz, 1H, 8 ax. H), 2.35 (ddd, J=2.0, 2.0, 15.0 Hz, 1H, 8 eq. H), 2.45 (s, 3H, CDCH$_3$), 2.92 (d, J=19 Hz, 1H, 10 ax. H), 3.17 (dd, J=2.0, 19.0 Hz, 1H, 10 eq. H), 3.74 (d, J=4.8 Hz, 1H, 7-OH), 4.54 (s, 1H, 9-OH), 5.32 (ddd, J=2.0, 4.8, 4.8 Hz, 1H, 7-H), 6.80 (broad, 2H, 4-NH$_2$), 6.93 (d, J=8.0 Hz, 1H, 3-H), 7.46 (t, J=8.0 Hz, 1H, 2-H), 7.64 (d, J=8.0 Hz, 1H, 1-H), 13.52 (s, 1H, 11-OH), 14.00 (s, 1H, 6-OH).

M.S.: m/z=383 (M+, base peak).

TLC on Kieselgel plate F 254 (Merck) using Chloroform/Acetone (8:2 by volume) Rf=0.50

To the solution of (6) in trifluoroacetic acid were added 2 L of methylene chloride and 700 mL of water, then, after cooling to 0° C., 0.93 g (13.5 mmol) of sodium nitrite were added. After stirring for 10 min. the aqueous phase was separated, washed once with 100 mL of methylene chloride and added with 300 mL of 50% hypophosphorous acid and 300 mL of methylene chloride. The reaction mixture was stirred at room temperature for one hour and then the phases were separated. The organic phase was washed with water, saturated NaHCO$_3$ and water, dried over sodium sulfate and the solvent evaporated "in vacuo" to give 1.61 g (4.37 mmoL) of 4-demethoxydaunomycinone (I) (HPLC 92%). Overall yield from daunomycinone 11.5%.

$^1$H-NMR 300 MHz (CDCl$_3$): δ=2.19 (dd, J=4.8, 14.5 Hz, 1H, 8 ax. H), 2.37 (ddd, J=2.0, 2.0, 14.5 Hz, 1H, 8 eq. H), 2.43 (s, 3H, COCH$_3$), 2.95 (d, J=18.6, 1H, 10 ax. H), 3.20 (dd, J=2.0, 18.6 Hz, 1H, 10 eq. H), 3.83 (d, J=4.8 Hz, 1H, 7-OH), 4.55 (s, 1H, 9-OH), 5.32 (ddd, J=2.0, 4.8, 4.8 Hz, 1H, 7-H), 7.84–7.86 (m, 2H, 2,3-H), 8.33–8.36 (m, 2H, 1,4-H), 13.30 (s, 1H, 6-OH), 13.60 (s, 1H, 11-OH).

U.V. spectrum (in EtOH): λ=208, 252, 257, 285, 480, 500, 514 nm., λmax =252 nm

I.R. spectrum (KBr pellet) υ=3450, 1715, 1625, 1585 cm$^{-1}$.

[α]$_D^{20}$ (C=0.1 in dioxane)= +156°

M.S.: m/z=368 (M$^+$, base peak)

TLC on Kieselgel plate F 254 (Merck) using Chloroform/Acetone (8:2 by volume) Rf=0.70.

We claim:

1. A process for the preparation of 4-demethoxydaunomycinone of formula (I):

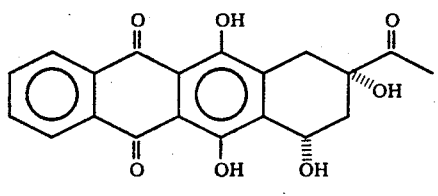

which process comprises:

(a) protecting the 13-keto group of 4-demethyldaunomycinone of formula (2):

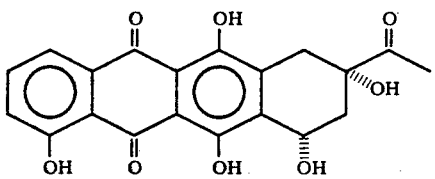

by treatment with ethylene glycol;

(b) reacting the resultant 4-demethyl-13-dioxolanyl-daunomycinone of formula (3):

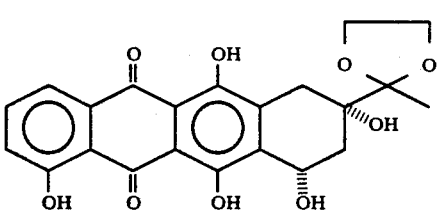

with a sulfonyl chloride of formula II:

R—SO$_2$Cl   (II)

wherein R represents an alkyl group of from 1 to 10 carbon atoms optionally substituted by one or more halogen atoms or an aryl group optionally substituted by halogen, alkyl, alkoxy or nitro, in the presence of N,N-diisopropylethylamine and a catalytic amount of 4-dimethylamino-pyridine.

(c) reacting the resultant sulfonated 4-demethyl-13-dioxolanyl-daunomycinone of formula (4):

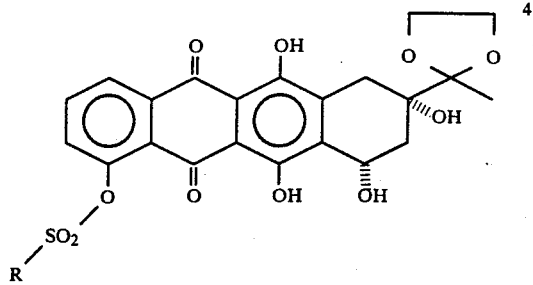

wherein R is as defined above, with an amine of formula III:

R$^1$(R$^2$)CH—NH$_2$   (III)

wherein R$^1$ and R$^2$ each independently represents a hydrogen atom or a phenyl group bearing one or more alkoxy groups;

(d) removing the amino protecting group from the resultant 4-demethyl-4-(protected amino)-13-dioxolanyl-daunomycinone of formula (5):

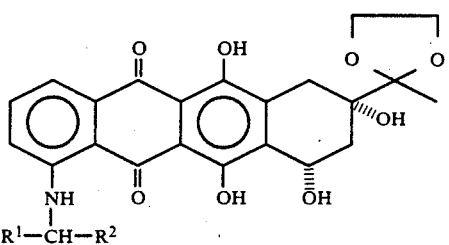

wherein R$^1$ and R$^2$ are as defined above;

(e) diazotising the 4-amino group of the resultant 4-demethoxy-4-amino-daunomycinone of formula (6):

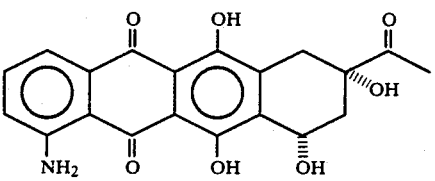

and (f) reducing the resultant diazo-derivative of formula (7):

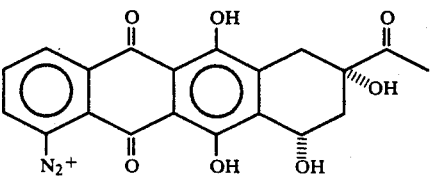

under mild conditions, thereby to obtain 4-demethoxydaunomycinone of formula I.

2. A process according to claim 1, wherein the 4-demethyl-daunomycinone of formula (2) has been prepared by demethylation of daunomycinone of formula (1):

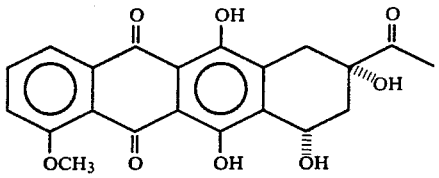

3. A process according to claim 2, wherein demethylation is effected by reflux with aluminium chloride in an inert organic solvent.

4. A process as claimed in claim 1, wherein step (a) is effected by treatment with ethylene glycol and p-toluenesulfonic acid in benzene at the reflux temperature.

5. A process as claimed in claim 1, wherein the sulfonyl chloride of formula (II) in step (b) is p-toluenesulfonyl chloride or 4-fluorophenylsulfonyl chloride.

6. A process as claimed in claim 1, wherein the amine of formula (III) in step (c) is 4-methoxybenzylamine or 3,4-dimethoxybenzylamine.

7. A process as claimed in claim 1, wherein step (d) is effected by reaction with trifluoroacetic acid.

8. A process as claimed in claim 1, wherein step (e) is effected using sodium nitrite.

9. A process as claimed in claim 1, wherein step (f) is effected using hypophosphorous acid.

10. A process for the preparation of 4-demethoxydaunomycinone of formula (I):

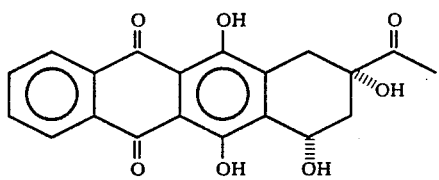

comprising:
(a) protecting the 13-keto group of 4-demethyldaunomycinone of formula (2):

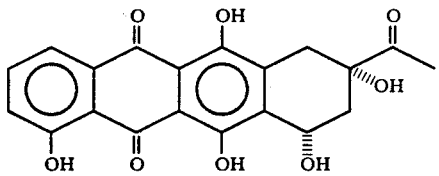

by treatment with ethylene glycol and p-toluenesulfonic acid, in benzene at the reflux temperature,
(b) reacting the resultant 4-demethyl-13-dioxolanyldaunomycinone of formula (3):

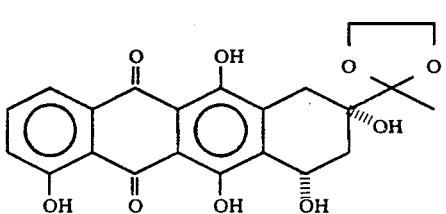

with an arenesulfonyl chloride selected from the group consisting of p-toluenesulfonyl chloride and 4-fluorophenylsulfonyl chloride, in the presence of N,N-diisopropylethylamine and a catalytic amount of 4-dimethylaminopyridine,
(c) reacting the sulfonated 4-demethyl-13-dioxolanyldaunomycinone of formula (4):

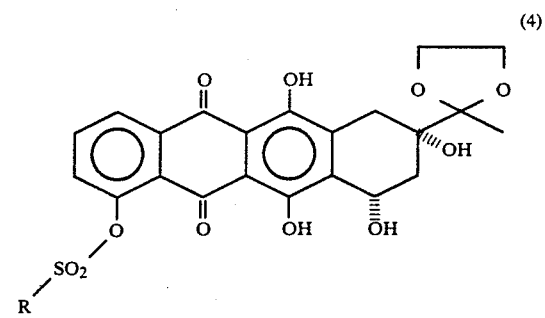

wherein R is selected from the group consisting of p-tolyl and 4-fluorophenyl, with an amine selected from the group consisting of 4-methoxybenzylamine and 3,4-dimethoxybenzylamine,
(d) removing the amino protecting group from the resultant 4-demethy-4-(protected amino)-13-dioxolanyldaunomycinone of formula (5):

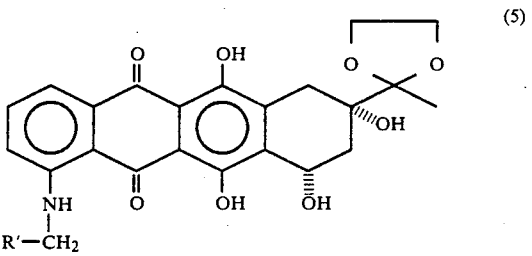

wherein $R^1$ is selected from the group consisting to 4-methoxyphenyl and 3,4-dimethoxyphenyl, by reaction with trifluoroacetic acid,
(e) diazotising the 4-amino group of the resultant 4-demethoxy-4-aminodaunomycinone of formula (6):

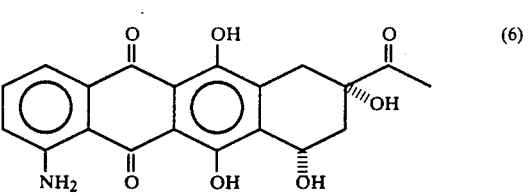

with sodium nitrite, and
(f) reducing the resultant 4-diazoniumdaunomycinone of formula (7):

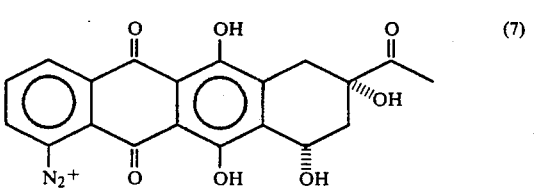

with hypophosphorous acid.

11. A process as claimed in claim 10, wherein said 4-demethyldaunomycinone of formula (2) is prepared by demethylation of daunomycinone of formula (1):

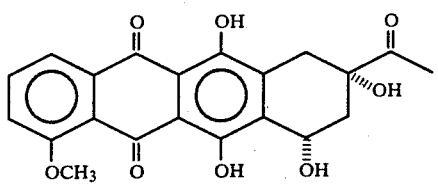
(1)
effected by aluminum chloride in an inert organic solvent heated to reflux.
* * * * *